(12) United States Patent
Lee et al.

(10) Patent No.: US 10,370,410 B2
(45) Date of Patent: Aug. 6, 2019

(54) CANCER CELL-TARGETING PEPTIDE AND USE THEREOF

(71) Applicant: KYUNGPOOK NATIONAL UNIVERSITY INDUSTRY-ACADEMIC COOPERATION FOUNDATION, Daegu (KR)

(72) Inventors: Byung-Heon Lee, Daegu (KR); Hyun-Kyung Jung, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 0 days.

(21) Appl. No.: 15/575,390

(22) PCT Filed: May 18, 2016

(86) PCT No.: PCT/KR2016/005256
§ 371 (c)(1),
(2) Date: Nov. 20, 2017

(87) PCT Pub. No.: WO2016/186445
PCT Pub. Date: Nov. 24, 2016

(65) Prior Publication Data
US 2018/0155394 A1    Jun. 7, 2018

(30) Foreign Application Priority Data
May 18, 2015 (KR) .......................... 10-2015-0069073

(51) Int. Cl.
C07K 7/06 (2006.01)
G01N 33/574 (2006.01)
A61K 31/704 (2006.01)
G01N 33/58 (2006.01)
A61K 47/42 (2017.01)
A61K 47/62 (2017.01)
A61K 47/69 (2017.01)
A61K 9/127 (2006.01)

(52) U.S. Cl.
CPC .............. *C07K 7/06* (2013.01); *A61K 31/704* (2013.01); *A61K 47/42* (2013.01); *A61K 47/62* (2017.08); *A61K 47/6911* (2017.08); *G01N 33/574* (2013.01); *G01N 33/57484* (2013.01); *G01N 33/58* (2013.01); *A61K 9/127* (2013.01)

(58) Field of Classification Search
CPC ....... C07K 7/06; G01N 33/574; A61K 31/704
See application file for complete search history.

(56) References Cited

FOREIGN PATENT DOCUMENTS

| KR | 10-2013-0091560 A | 8/2013 |
|---|---|---|
| KR | 10-1467676 B1 | 12/2014 |
| KR | 10-1471253 B1 | 12/2014 |

OTHER PUBLICATIONS

Fraser et al., 1998, Complete Genome Sequence of Treponema pallidum, the Syphilis Spirochete, Science, 281: 375-388.*
Callol et al., 2015, Early steps in the European eel (*Anguilla anguilla*)—Vibrio vulnificus interaction in the gills: Role of the RtxA13 toxin, Fish and Shellfish Immunology, 43: 502-509.*
International Search Report for PCT/KR2016/005256 dated Aug. 26, 2016 from Korean Intellectual Property Office.
NCBI, GenBank accession No. WP_018087053.1 (Jun. 28, 2013).
NCBJ, GenBank accession No. KKA25050.1 (Apr. 3, 2015).
NCBI, GenBank accession No. EZA56312.1 (Apr. 8, 2014).
NCBI, GenBank accession No. CDJ30333.1 (Nov. 5, 2013).

* cited by examiner

*Primary Examiner* — Amber D Steele
(74) *Attorney, Agent, or Firm* — Revolution IP, PLLC

(57) ABSTRACT

The present invention relates to a peptide targeting a tumor cell and use of the peptide, and more particularly, to a peptide consisting of SEQ ID NO: 1 to SEQ ID NO: 4 and specifically binding to a tumor cell, a composition including the peptide as an effective ingredient for detecting a tumor cell, a composition including the peptide as an effective ingredient for delivering a drug, and a composition including the peptide as an effective ingredient for imaging. The peptide of the present invention can be used for detection or imaging of a tumor cell in vitro and in vivo by specifically binding to a tumor cell.

10 Claims, 9 Drawing Sheets

Specification includes a Sequence Listing.

[FIG. 1]
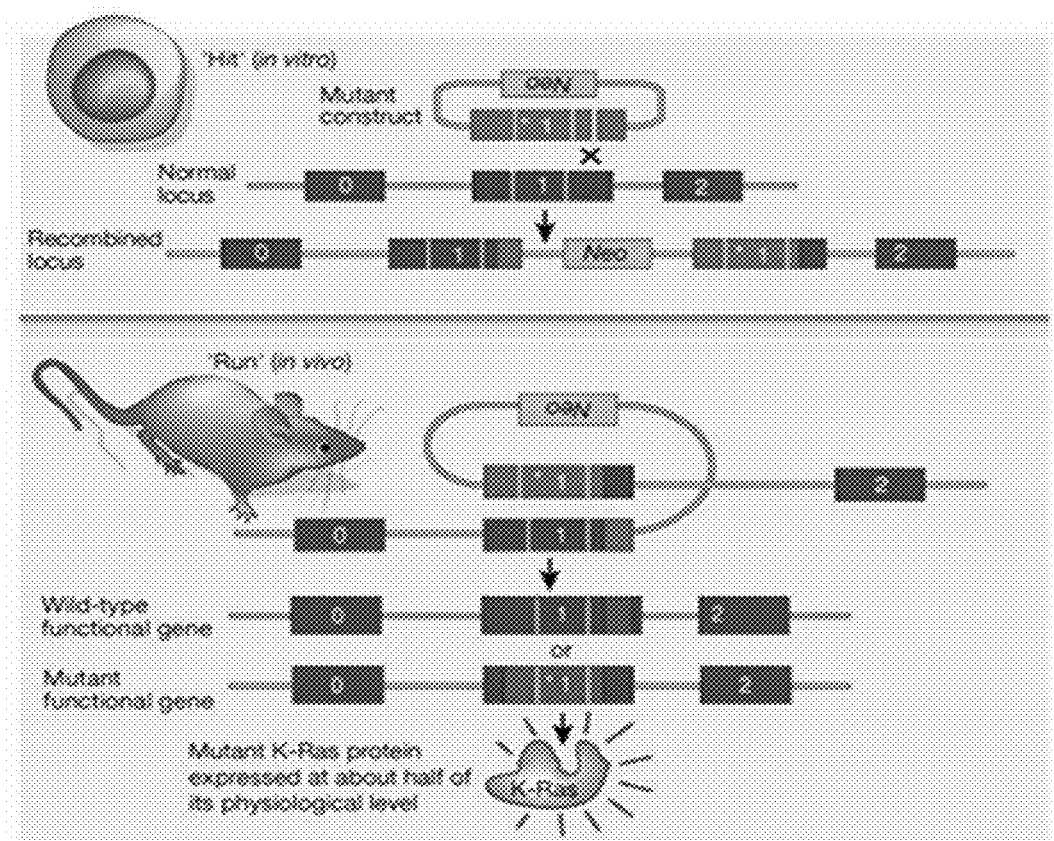

[FIG. 2]
A
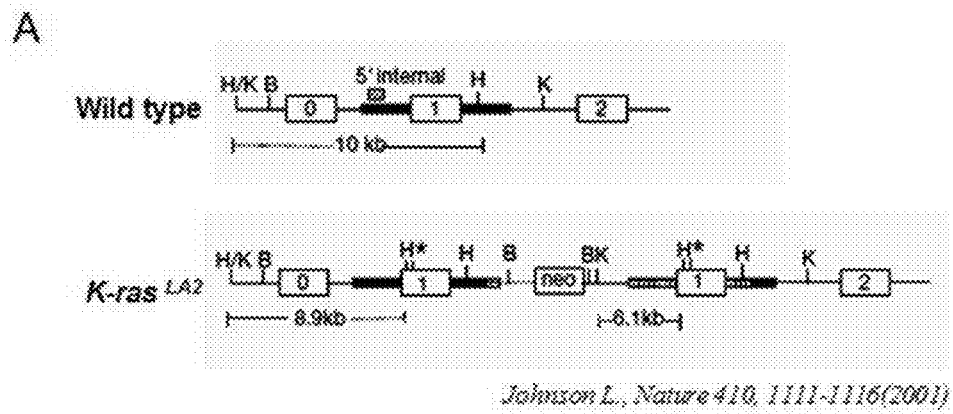
B
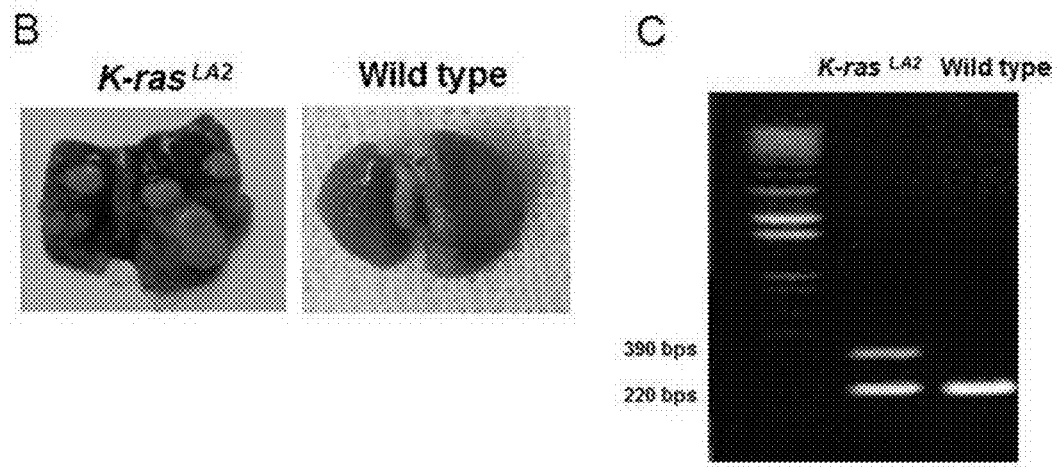

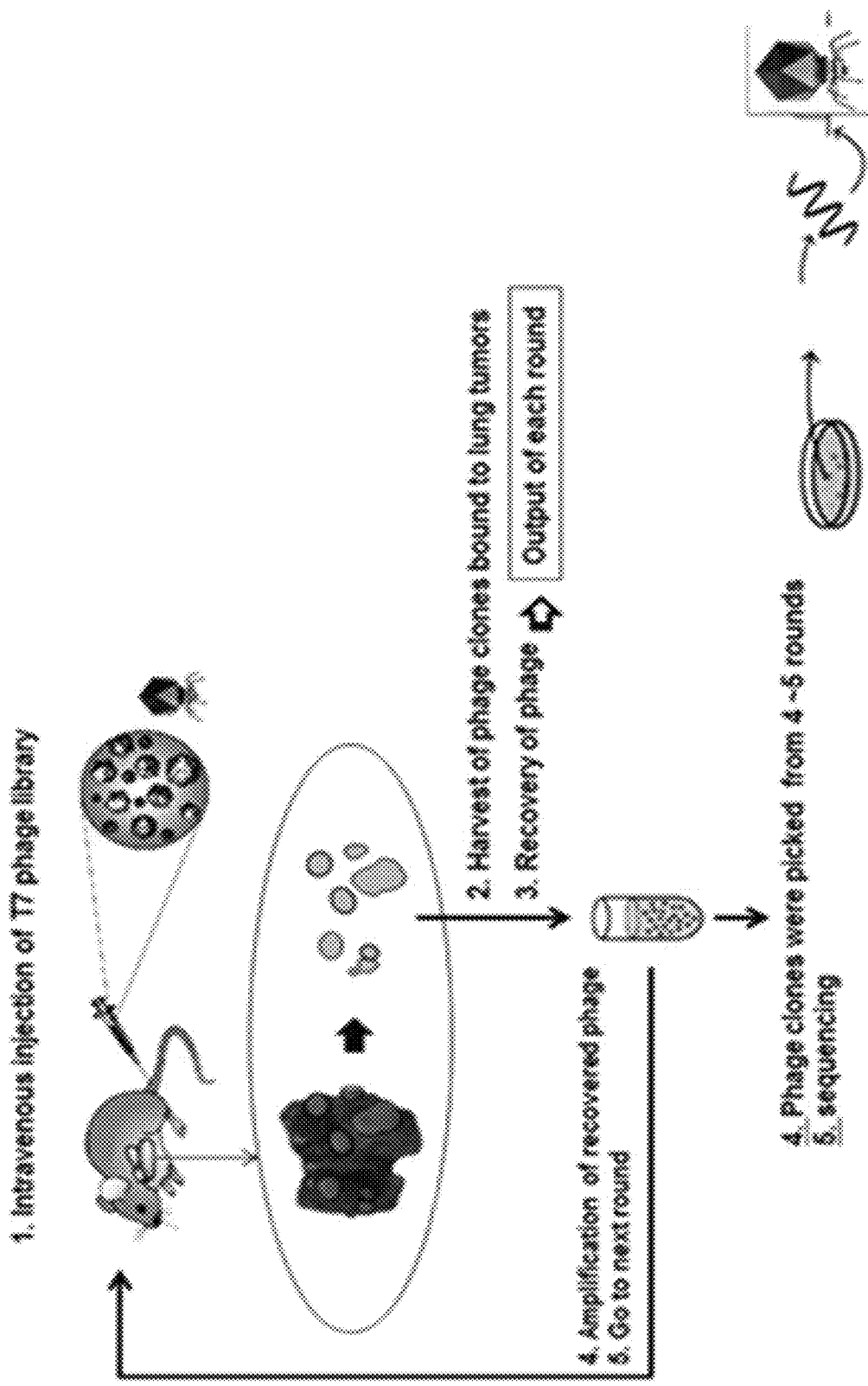
[FIG. 3]

[FIG. 4]
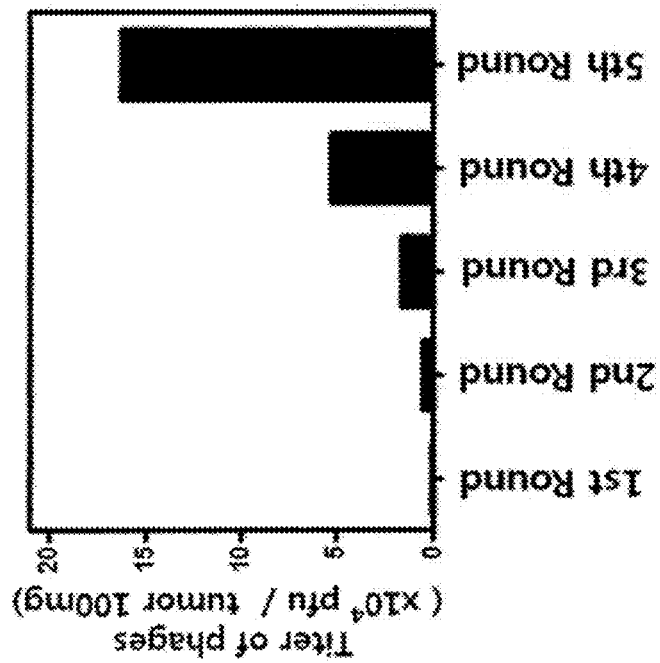
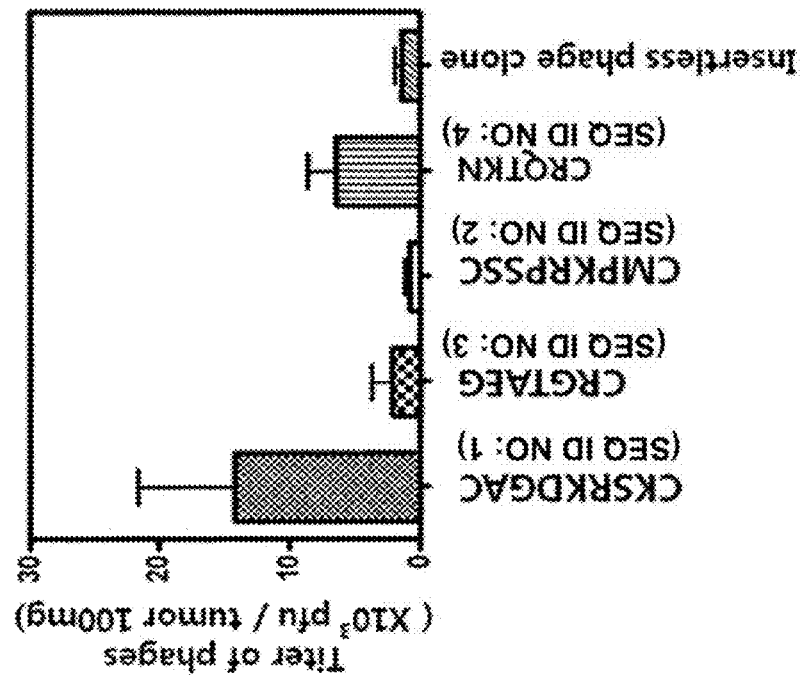

[FIG. 5]
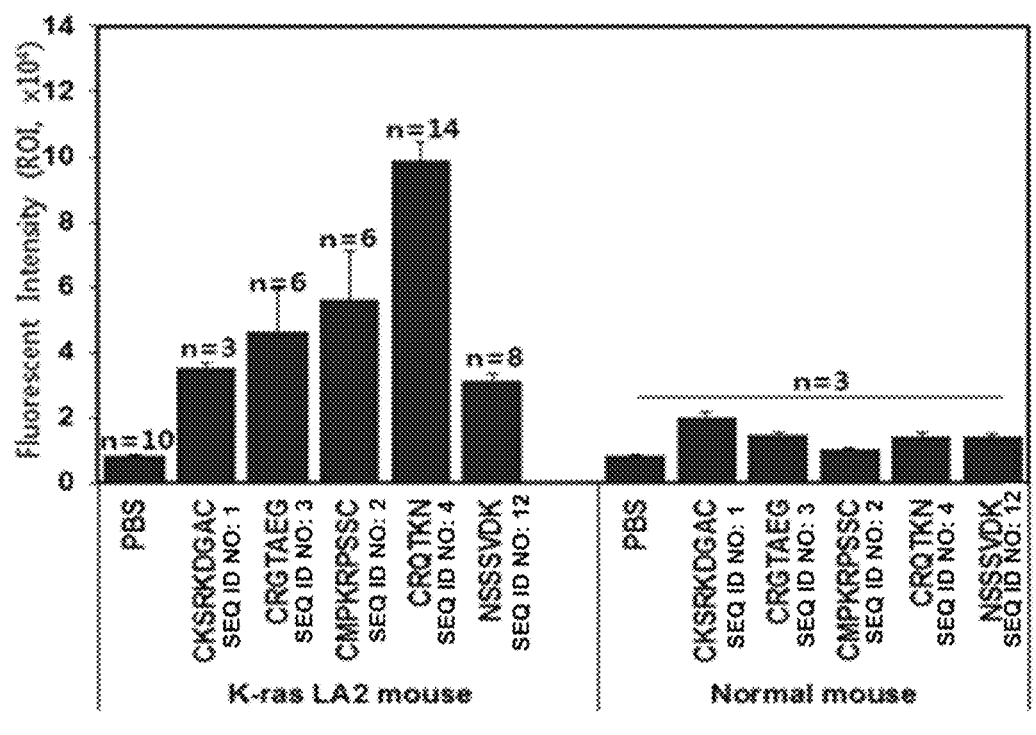

[FIG. 6]
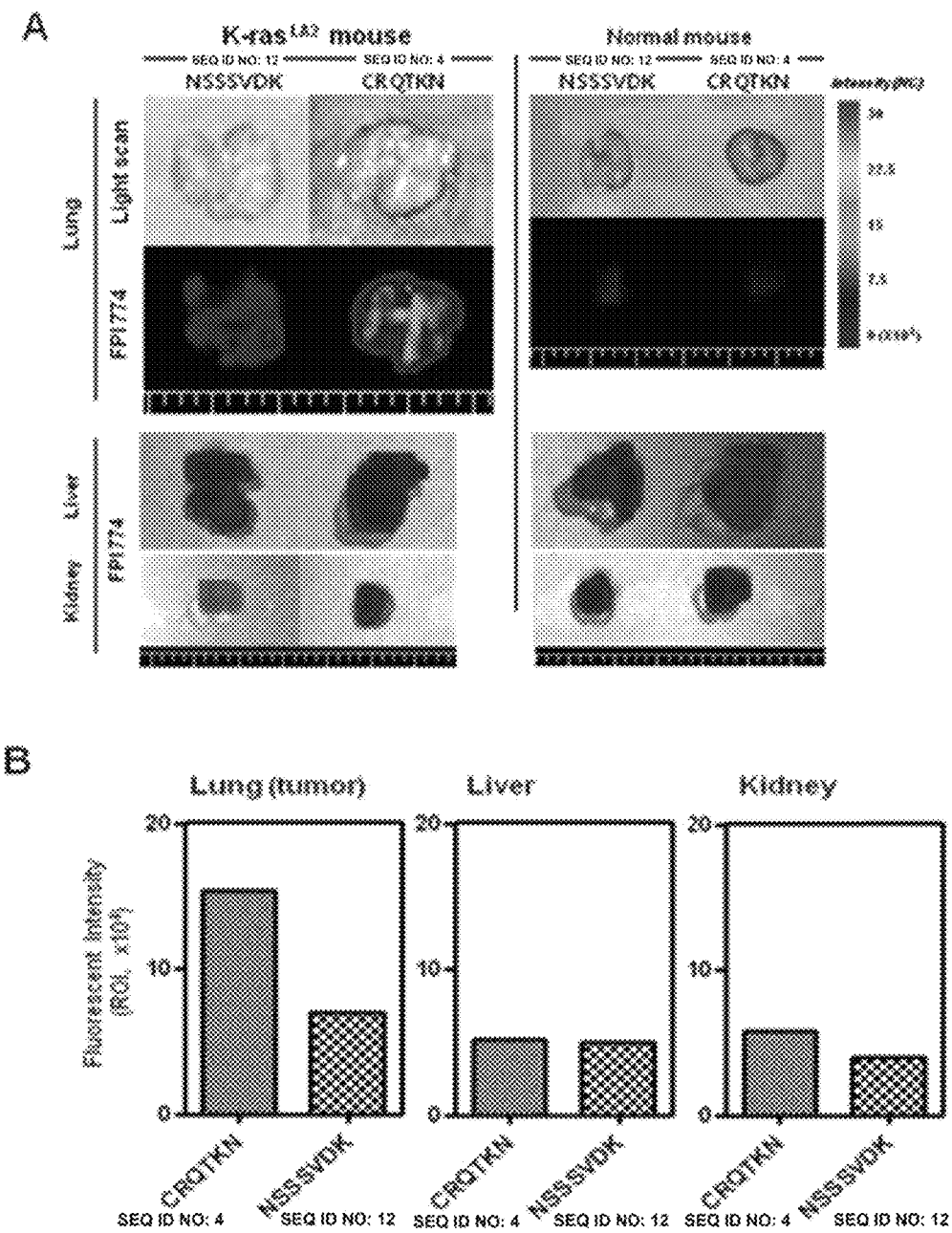

[FIG. 7]
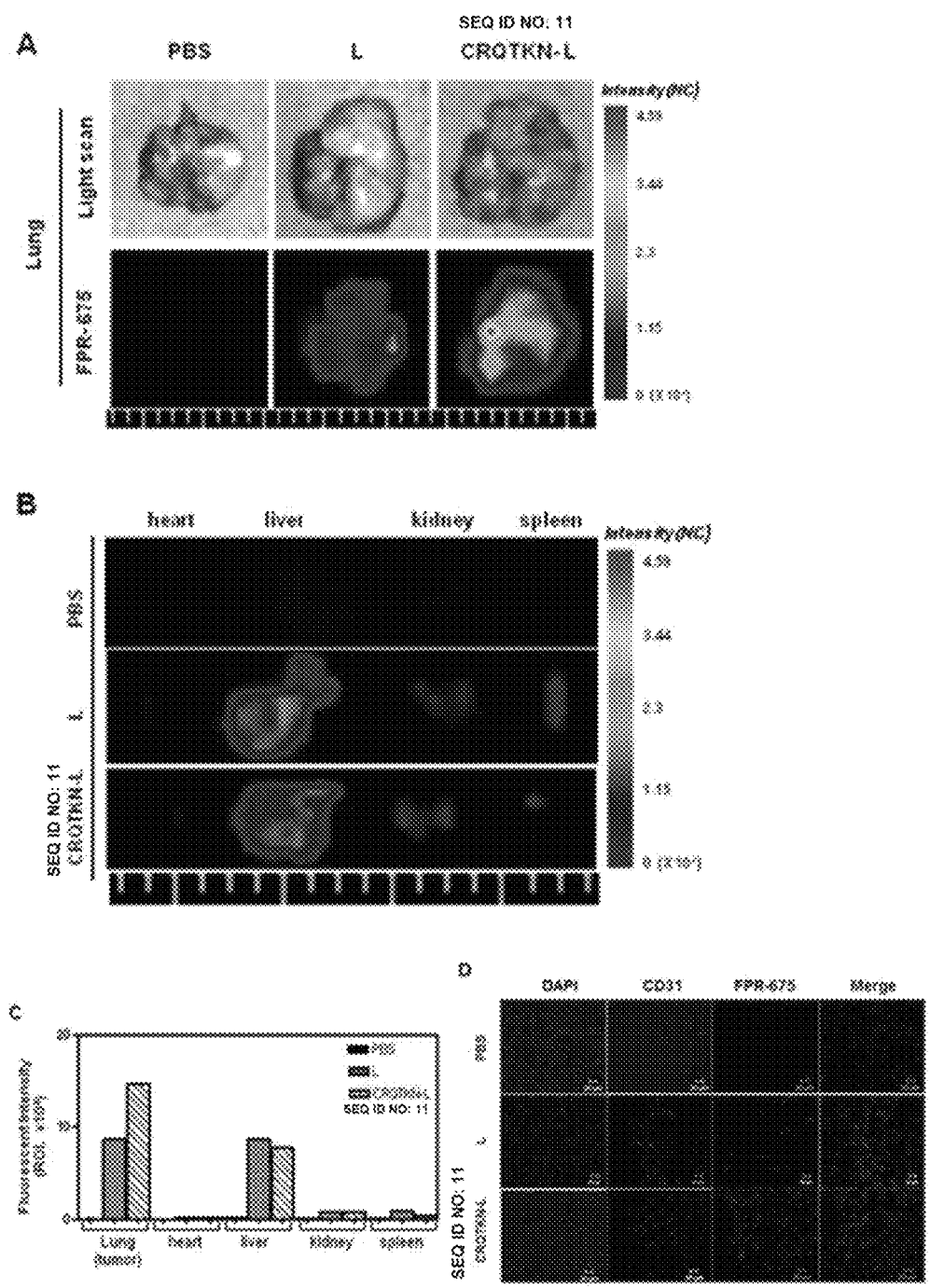

[FIG. 8]
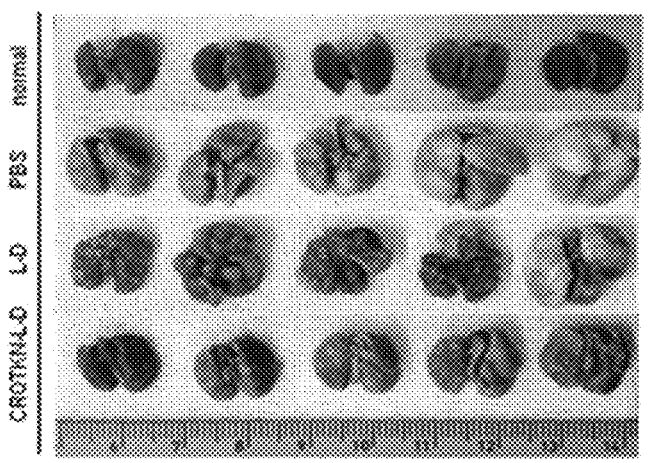
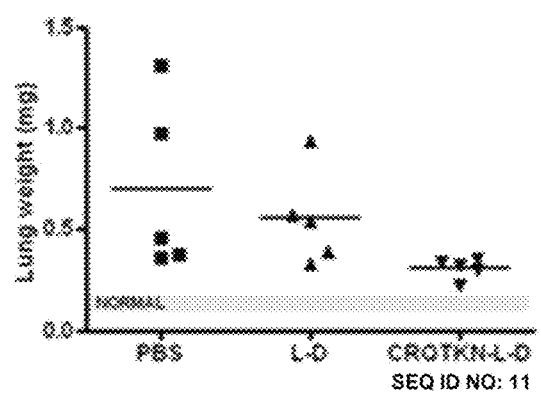
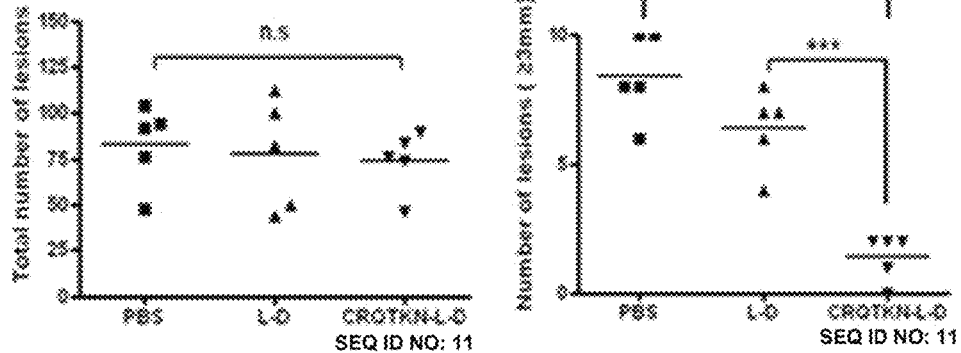

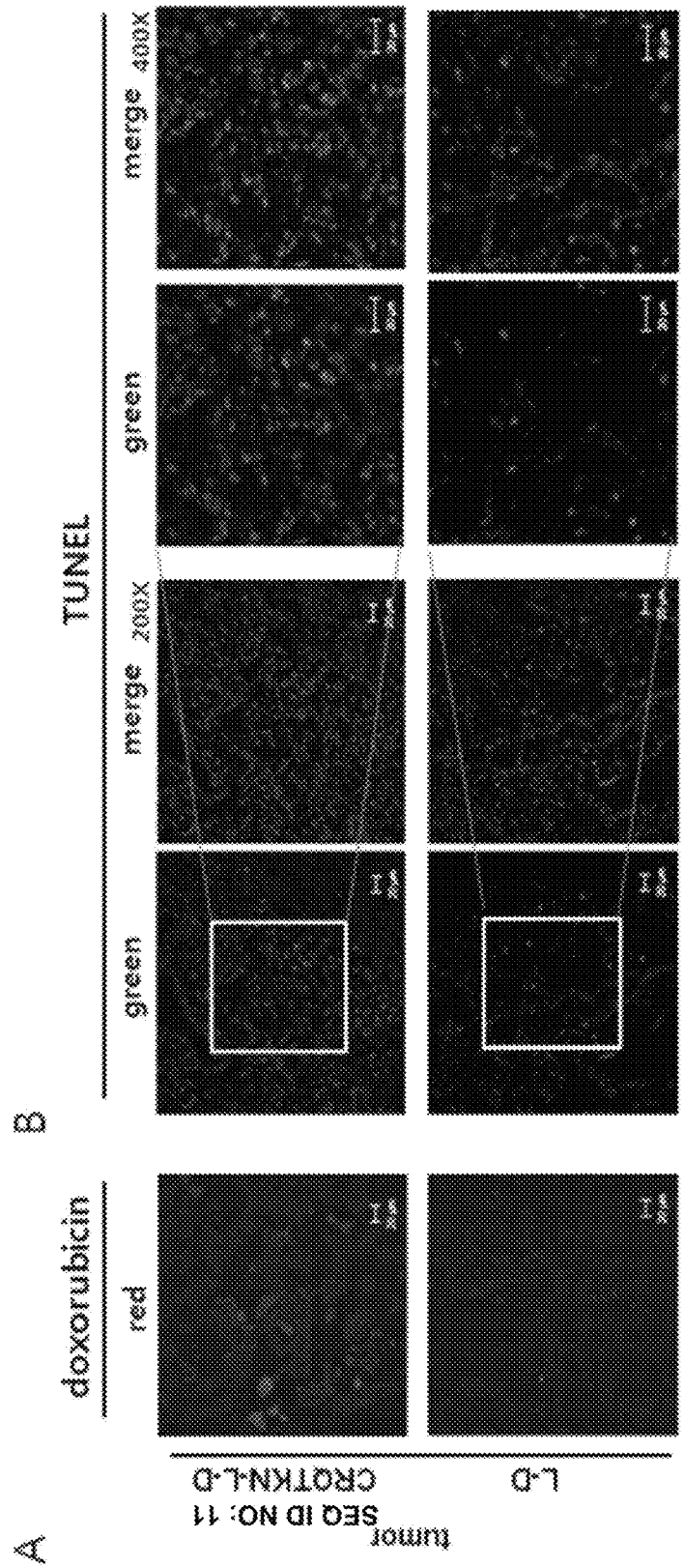
[FIG. 9]

CANCER CELL-TARGETING PEPTIDE AND USE THEREOF

TECHNICAL FIELD

The present application claims priority to Korean Patent Application No. 10-2015-0069073 filed on May 18, 2015, which is hereby incorporated by reference herein.

The present invention relates to a peptide targeting a tumor cell and use of the peptide, and more particularly, to a peptide specifically binding to a tumor cell and consisting of SEQ ID NO: 1 to SEQ ID NO: 4, a composition including the peptide as an effective ingredient for detecting a tumor cell, a composition including the peptide as an effective ingredient for delivering a drug, and a composition including the peptide as an effective ingredient for imaging.

BACKGROUND ART

Cancer is one of the most common diseases in the world, and treatments that are currently being performed are surgery, radiotherapy, and chemotherapy. Although molecular mechanisms of cancer have been actively studied, many of the currently developed therapies rely on surgical procedures. Recently, however, a variety of targeted therapeutic agents, such as a small molecule inhibitor, a monoclonal antibody, and a short tumor cell-targeting peptide, have been developed and used as therapeutic agents (Corti A et al., Blood. 2008; 112:2628-35). In particular, a short targeting peptide is highly permeable to a tissues and has low toxicity and immune responses, making them highly effective as an effective anticancer agent (Yang W et al., Clin Cancer Res. 2008; 14:5494-02).

A phage display technique using peptides and proteins is a very useful method of identifying ligands specific to target cells and is a method that has been widely used to discover peptides and proteins that target tumor cells in vitro and in vivo. Representatively, in in vivo phage screening in a phage library of mouse models, RGD, GSL, and NGR motifs are specifically bound to integrin which is activated in epithelial tumors where angiogenesis is activated, VGF receptor, MMP, or the like (Pasqualini R et al., Ann Hematol. 2002; 81: S66-S67), and are found to be expressed in IL11 receptors of prostate blood vessels and microvessels of breast cancer (Arap W et al., Proc. Natl. Acad. Sci. USA. 2002; 1527-31). However, these study results do not provide a phage that can selectively identify patterns appearing transiently at the stage where early tumors are progressed to malignant tumors. Therefore, there is a need to develop peptides and proteins that targets what is specifically expressed at each stage of tumor cells.

A drug system or target therapy that delivers a drug selectively to a tumor has attracted a great deal of attention, because use of the same amount of anticancer drugs can increase the efficacy of the drug, and at the same time, can significantly reduce side effects on normal tissues. In addition, when applied to the gene therapy, virus can be selectively delivered to tumor cells, so as to increase treatment efficiency and reduce serious side effects. To date, antigens that are specific to tumor cells and antibodies that target the antigens have been mainly developed. However, in case of antibodies, there are problems such as concerns of immune response and low efficiency of penetration into tissues. In case of peptides, small molecular weights thereof reduce concerns of immune response and there are advantages of easy transmission into tissues. Therefore, when linking cancer-targeting peptides to existing anticancer drugs, such cancer-targeting peptides can be utilized as drug delivering materials that delivers a drug selectively to tumor. In this regard, there is a need to develop a cancer-targeting peptide.

DETAILED DESCRIPTION OF THE INVENTION

Technical Problem

The inventors of the present disclosure discovered a peptide capable of targeting specifically a tumor cell in in-vitro (and ex-vivo) and in vivo, and confirmed that such a peptide was effective in detecting and imaging a tumor cell in in vitro and in vivo, thereby completing the present disclosure.

Therefore, the present disclosure is to provide a peptide specifically binding to a tumor cell, the peptide consisting of an amino acid sequence selected from the group consisting of SEQ ID NO: 1 to SEQ ID NO: 4, and to provide use of the peptide.

Technical Solution

To achieve the technical problems above, the present disclosure provides a peptide targeting a tumor cell, the peptide consisting of an amino acid sequence selected from the group consisting of SEQ ID NO: 1 to SEQ ID NO: 4.

To achieve the technical problems above, the present disclosure provides a polynucleotide including a nucleotide sequence that encodes the peptide.

To achieve the technical problems above, the present disclosure provides a vector including the polynucleotide.

To achieve the technical problems above, the present disclosure provides a transformants transformed with the vector.

To achieve the technical problems above, the present disclosure provides a composition including the peptide as an effective ingredient for detection of a tumor cell.

To achieve the technical problems above, the present disclosure provides a method of detecting a tumor cell, the method including: (a) mixing the peptide with a sample; (b) removing the peptides that are unbound or non-specifically bound; and (c) determining whether or not the peptide is bound or not and a binding position of the peptide.

To achieve the technical problems above, the present disclosure provides a composition including the peptide as an effective ingredient for a delivery of a drug specifically to a tumor cell.

To achieve the technical problems above, the present disclosure provides a composition including the peptide as an effective ingredient for imaging a tumor cell.

To achieve the technical problems above, the present disclosure provides a composition including, as effective ingredients, the peptide and an anticancer drug binding thereto.

To achieve the technical problems above, the present disclosure provides a method of treating cancer, the method including: administering a subject with an effective amount of a peptide that targets a tumor cell and consists of an amino acid selected from the group consisting of SEQ ID: 1 to SEQ ID NO:4, and a method of treating cancer, the method including: administering a subject with an effective amount of an antibody agent binding thereto.

To achieve the technical problems above, the present disclosure provides use of a peptide targeting a tumor cell for use in preparing an anticancer agent, the peptide consisting of an amino acid selected from the group consisting of SEQ ID NO:1 to SEQ ID NO: 4.

Hereinafter, the present disclosure will be described in detail.

The term "peptide" as used herein can be used interchangeable with "a protein" or "a polypeptide". For example, a peptide may refer to a polymer of amino acid residues that are proteins generally found in a natural state.

The term "polynucleotide" or "nucleic acid" as used herein refers to a single-stranded or double-stranded deoxyribonucleotide or ribonucleotide. Unless there are other limitations, in a similar method of a naturally produced nucleotide, the polynucleotide or nucleic acid includes an analog thereof known in a natural nucleotide hybridized to nucleic acid.

The term "expression" as used herein refers to production of proteins or nucleic acids in a cell.

The term "tumor" as used herein refers to a physiological state of mammals with the characteristics of uncontrolled cell growth/proliferation, and can be used as a replacement for cancer. Examples of the tumor include carcinoma, lymphoma (for example, Hodgkin and non-Hodgkin lymphoma), blastoma, sarcoma, and leukemia, but embodiments of the disclosure are not limited thereto. More specific examples of the tumor include squamous carcinoma, small cell lung cancer, non-small cell lung cancer, lung adenocarcinoma, lung squamous carcinoma, peritoneal cancer, hepatocellular carcinoma, gastrointestinal malignancy, pancreatic cancer, glioma, cervical cancer, ovarian cancer, liver cancer, bladder cancer, liver cancer, breast cancer, colon cancer, colorectal cancer, endometrium or cervical carcinoma, salivary gland carcinoma, renal cancer, liver cancer, prostate cancer, vulvar cancer, thyroid cancer, hepatocarcinoma, leukemia and other lymphoproliferative disorders, and various types of head and neck cancer. Tumor in the present disclosure may preferably refer to lung cancer, pancreatic cancer, colon cancer, bile duct cancer, gallbladder cancer, or blood cancer, and more preferably, refer to lung cancer or blood cancer.

The term "K-ras" as used herein refers to a carcinogenic gene derived from a rat with Kirsten mouse sarcoma virus (Ki-MSV). It has been studied that mutations of the K-ras gene in some solid cancers of humans have a significant relationship with cell carcinogenesis.

The single codon (triplet codon) of amino acids as used herein refers to the following amino acids in accordance with the standard abbreviations in the field of biochemistry.

A(Ala): alanine; C(Cys): cystein; D(Asp): aspartic acid; E(Glu): glutamic acid; F(Phe): phenylalanine; G(Gly): glycine; H(His): histidine; I(Ile): isoleucine; K(Lys): lysine; L(Leu): leucine; M(Met): methionine; N(Asn): asparagine; O(Ply): pyrrolysine; P(Pro): proline; Q(Gln): glutamine; R(Arg): arginine; S(Ser): serine; T(Thr): threonine; U(Sec): selenocysteine, V(Val): valine; W(Trp): tryptophan; and Y(Tyr): tyrosine.

The present invention provides a peptide targeting a tumor cell, the peptide consisting of one amino acid sequence selected from the group consisting of SEQ ID NO: 1 to SEQ ID NO: 4.

Each of peptides represented by SEQ ID NO: 1 to SEQ ID NO: 4 specifically binds to a tumor cell, and preferably, the peptide of the present invention consists of an amino acid sequence of SEQ ID NO: 4.

As described above, the peptide of the present invention consisting of a specific combination of amino acid sequences specifically targets a tumor cell and binds to a cell membrane of a tumor cell.

The tumor cell-specific peptide of the present invention can be applied to various types of tissues and cells in vitro and in vivo, and can provide accurate information on cancer.

In the present invention, a tumor cell may be a tumor cell caused by K-ras mutation, and more particularly, may refer to a lung cancer cell, a pancreatic cancer cell, a colon cancer cell, a bile duct cancer cell, or a gallbladder cancer cell. More particularly, a tumor cell in the present invention may refer to a lung cancer cell.

Effects of such peptide are well described in Examples in the present specification.

In one embodiment of the present invention, four types of peptides that specifically bind to a tumor cell, i.e., CKSRKDGAC (4R-3, SEQ ID NO: 1), CMPKRPSSC (4R-16, SEQ ID NO: 2), CRGTAEG (4R-21, SEQ ID NO: 3), and CRQTKN (5R-7, SEQ ID NO: 4), are identified by phage library screening (see Example 2), and then, binding specificity of these peptides to a cancer cell is examined (see Example 3). As a result, it is confirmed that the peptides of the present invention are not found in organs, such as liver and spleen, where a cancer cell does not exist, whereas the peptides of the present invention are found in the lungs where a cancer cell exists. That is, it is confirmed that the peptides of the present invention specifically binds to a tumor cell. In addition, the peptides of the present inventions can be used to perform imaging a cancer cell not only in in vitro experiments, but also in in vivo experiments on ischemia-reperfusion (IR) animal models (see Example 4).

The peptides of the present invention may be derived from natural sources, and may be also synthesized using known peptide synthesis methods (e.g., genetic engineering method, chemical synthesis method, etc). The genetic engineering methods are used to prepare, for example, nucleic acids (for example, polynucleotides of SEQ ID NO: 5 to SEQ ID NO: 8) that encode the peptides of the present invention or functional equivalents thereof according to conventional methods. These nucleic acids can be prepared by PRC amplification using appropriate primers. Regarding other methods, the standard methods known in the art using an automated DNA synthesizer (sold by Biosearch or Applied Biosystems Company) may be used to synthesize DNA sequences. The prepared nucleic acids are operably linked and inserted into a vector including one or more expression control sequences (for example, a promoter, an enhancer, etc) that control the expression of the nucleic acids. Then, a host cell may be transformed with a recombinant expression vector prepared therefrom. The resulting transformant is cultured in a suitable medium under appropriate conditions for the expression of nucleic acids, and then, substantially pure peptides that are expressed by the nucleic acids are recovered from the culture. Such recovery can be carried out using methods known in the art (for example, chromatography). The term "substantially pure peptides" as used herein refers that the peptides of the present invention do not substantially include any other proteins derived from the host cell. The genetic engineering methods for the peptides of the present invention can be referred to the following references: Maniatis et al., Molecular Cloning; A laboratory Manual, Cold Spring Harbor laboratory, 1982; Sambrook et al., Molecular Cloning: A Laboratory Manual, Cold Spring Harbor Press, N.Y., Second (1998); and Third (2000) Editions; Gene Expression Technology, Method in Enzymology, Genetics and Molecular Biology, Method in Enzymology, Guthrie Fink (eds.), Academic Press, San Diego, Calif., 1991; and Hitzeman et al., J. Biol. Chem., 255:12073-12080, 1990.

In addition, the peptides of the present invention can be easily prepared according to the chemical synthesis methods known in the art (Creighton, Proteins; Structures and Molecular Principles, W. H. Freeman and Co., NY, 1983). Representative methods, although not limited thereto, include liquid or solid phase synthesis, fractional condensation, F-MOC or T-BOC chemistry, and the like (Chemical Approaches to the Synthesis of Peptides and Proteins, Williams et al., Eds., CRC Press, Boca Raton Fla., 1997; A Practical Approach, Athert on Sheppard, Eds., IRL Press, Oxford, England, 1989).

In addition, the peptides of the present invention include not only peptides having naturally occurring amino acid sequences, but also amino acid sequence mutants thereof. The mutants of the peptides of the present invention include peptides having different sequences by deletion, insertion, and non-conservative or conservative substitution of at least one amino acid residue in the amino acid sequence of the present invention, substitution of an amino acid analog, or any combination thereof. The exchange of amino acids without changing the molecular activity overall is already known in the art (H. Neurath, R. L. Hill, The Proteins, Academic Press, New York, 1979)

According to circumstances, the peptides of the present invention may be subjected to modification, such as phosphorylation, sulfation, acrylation, glycosylation, methylation, and farnesylation.

The present invention provides a polynucleotide including a nucleotide sequence that encodes the peptides.

In the polynucleotide, a nucleotide combination is not particularly limited as long as it can encode the peptides of the present invention. The polynucleotide may be provided as a nucleic acid molecule in the form of a short chain or double chain including DNA, cDNA, and RNA.

Preferably, the polynucleotide of the present invention may be a polynucleotide that encodes any one of the peptides selected from the group consisting of SEQ ID NO: 1 to SEQ ID NO: 4, and for example, may have one nucleotide sequence selected from the group consisting of SEQ ID NO: 5 to SEQ ID NO: 8. In detail, a polynucleotide encoding the peptide of SEQ ID NO: 1 may consist of a nucleotide sequence of SEQ ID NO: 5, a polynucleotide encoding the peptide of SEQ ID NO: 2 may consist of a nucleotide sequence of SEQ ID NO: 6, a polynucleotide encoding the peptide of SEQ ID NO: 3 may consist of a nucleotide sequence of SEQ ID NO: 7, and a polynucleotide encoding the peptide of SEQ ID NO: 4 may consist of a nucleotide sequence of SEQ ID NO: 8, but embodiments of the present invention are not limited thereto.

The present invention provides a vector including the polynucleotide.

The vector of the present invention includes a plasmid vector, a cosmid vector, a bacteriophage vector, and a viral vector, but embodiments of the present invention are not limited thereto. The vector of the present invention may be a conventional cloning vector or an expression vector. The expression vector may be variously prepared depending on the purpose, and include not only expression control sequences, such as a promoter, an operator, an initiation codon, a stop codon, a polyadenylation signal, and an enhance (promoter), but also a signal sequence or a leader sequence for film targeting or secretion. The polynucleotide sequence of the present invention may be operably linked to the expression control sequences, and the operably linked gene sequences and expression control sequences may be contained in an expression vector including a selection marker and a replication origin together. The term "operably linked gene sequence and expression control sequences" as used here refers to gene sequences and expression control sequences that are linked in such a way that allows gene expression when an appropriate molecule is linked to the expression control sequences. The term "expression control sequences" as used herein refers to DNA sequences that control the expression of the polynucleotide operably linked in a specific host cell, and such control sequences include a promoter for conducting transcription, any operator sequences for controlling transcription, a sequence encoding an appropriate mRNA ribosome-binding site, and a sequence for controlling termination of transcription and translation. In addition, the vector may include a selection market for selecting a vector-containing host cell, and in the case of a replicable vector, the vector may include a replication origin.

The present invention provides a transformant transformed with the vector.

The transformation with the vector may be performed by transformation techniques known in the art. Preferably, microprojectile bombardment, electroporation, calcium phosphate (CaPO4) precipitation, calcium chloride ($CaCl_2$) precipitation, PEG-mediated fusion, microinjection, and liposome-mediated method may be used.

The term "transformant" as used herein may be used interchangeably with a host cell or the like, and refers to prokaryotic or eukaryotic cells including heterologous DNA introduced into cells by any means (for example, electroporation, calcium phosphatase precipitation, microinjection, transformation, virus infection, etc).

In the transformant of the present invention, a host cell derived from all types of single-celled organism conventionally used in the field of cloning, such as prokaryotic microorganisms including various bacteria (for example, *Clostridia* spp., *Escherichia coli*, etc), low eukaryotic microorganisms such as yeast, and high eukaryotes including insect cells, plant cells, and mammals can be used, but embodiments of the present invention are not limited thereto. Depending on a host cell, the expression amount of proteins and the expression equation are different. Thus, a host cell most suitable for those skilled in the art can be selected and used. For example, a microorganism used as the transformant include *Escherichia coli, Bacillus subtilis, Streptomyces* spp., *Pseudomonas* spp., *Proteus mirabilis, Staphylococcus* spp., *Agrobacterium tumefaciens*, or the like, but embodiments of the present invention are not limited thereto.

The present invention provides a composition for detecting a tumor cell, the composition including the peptide as an effective ingredient.

Preferably, the present invention provides a composition for detecting a tumor cell, the composition including the peptide consisting of any one amino acid sequence selected from SEQ ID NO: 1 to SEQ ID NO: 4.

The tumor cell in the present invention may be a tumor cell caused by K-ras mutation, and more particularly, may refer to a lung cancer cell, a pancreatic cancer cell, a colon cancer cell, a bile duct cancer cell, or a gallbladder cancer cell. More particularly, a tumor cell in the present invention may refer to a lung cancer cell.

To facilitate determination of the tumor cell binding, detection, and quantification of the peptides of the present invention, the peptides of the present invention may be provided in a labeled state. That is, the peptides of the present invention may be provided with a detectable label linked (for example, via covalent bonding or cross-linking) thereto. The detectable label may be a chromogenic enzyme (for example, peroxidase, alkaline phosphatase, etc), a radioisotope (for example, $^{18}F$, $^{123}I$, $^{124}I$, $^{125}I$, $^{32}P$, $^{35}S$, $^{67}Ga$, etc), a chromophore, a luminescent or fluorescent substance (for example, FITC, RITC, green fluorescent protein (GFP), enhanced green fluorescent protein (EGFP), red fluorescent protein (RFP), *discosoma* sp. red fluorescent protein (DsRed), cyan fluorescent protein (CFP), cyan green fluorescent protein (CGFP), yellow fluorescent protein (YFP), Cy3, Cy5, Cy7.5, etc), or a magnetic resonance imaging substance (for example, gadolinium (Gd), super paramagentic particles or ultrasuper paramagentic particles, etc).

The detection method using labeling is widely known in the art, but can be performed by, for example, the following method. When a fluorescent substance is used as a detectable label, an immunofluorescent staining method may be used. For example, the peptides of the present invention that are labeled with a fluorescent substance may be reacted with a sample, and then, fluorescence of the peptides can be observed under a fluorescence microscope after removing unbound or non-specific binding products. In addition, when an enzyme is used as a detectable label, the absorbance can be measured by a color reaction of a substrate through an enzyme reaction. When a radioactive substance is used as a detectable label, the emission amount of radiation can be measured. Furthermore, the results obtained by the detection may be imaged according to a known imaging method based on the detected label.

The present invention provides a method of detecting a tumor cell, the method including: (a) mixing the peptide with a sample; (b) removing the peptide that is unbound or non-specifically bound; and (c) determining whether or not the peptide is bound and a binding position of the peptide.

In the step (c), a peptide detection method used for determining whether or not the peptide of the present invention is bound to a tumor cell and a binding position of the peptide can be performed according to the method described above or a known method in the art.

The term "sample" as used herein refers to a biological sample, and includes blood and other liquid samples of biological origin, a biopsy sample, a solid tissue sample such as a tissue culture, or a cell derived from the solid tissue sample. The sample may be obtained from an animal, preferably, a mammal. The sample may be pretreated prior to use for detection. For example, the pretreatment may include extraction, concentration, inactivation of interfering components, or addition of reagents.

In addition, due to excellent tumor cell-specific binding capability of the peptides of the present invention, the peptides can be used as intelligent drug delivery vehicles that selectively deliver a drug to the tumor cell (eventually, to a diseased site where K-ras tumor cells are present in vivo).

In the present invention, a tumor cell may be a tumor cell caused by K-ras mutation, and more particularly, may refer to a lung cancer cell, a pancreatic cancer cell, a colon cancer cell, a bile duct cancer cell, or a gallbladder cancer cell. More particularly, a tumor cell in the present invention may refer to a lung cancer cell.

The present invention provides a composition for delivering a drug specifically to a tumor cell, the composition including the peptide as an effective ingredient.

The composition for delivering a drug of the present invention can deliver a drug specifically to a tumor cell, wherein types of the tumor are not particularly limited. However, preferably, the tumor may be tumor caused by K-ras mutation, and more particularly, may be lung cancer, pancreatic cancer, colorectal cancer, bile duct cancer, gallbladder cancer, or leukemia.

In particular, when the peptide of the present invention included in the composition for delivering a drug is linked to an agent such as a conventional antitumor (anticancer) agent for treatment, due to the peptide of the present invention, the agent can be selectively delivered to a tumor cell, thereby increasing the efficacy of the drug, and at the same time, significantly reducing side effects on normal tissues.

As the antitumor agent that can be linked to the peptide of the present invention, types of the antitumor agent are not particularly limited as long as it is a known tumor therapeutic agent. The antitumor agent may include at least one selected from the group consisting of paclitaxel, doxorubicin, vincristine, daunorubicin, vinblastine, actinomycin-D, docetaxel, etoposide, teniposide, bisantrene, homoharringtonine, Gleevec (STI-571), cisplain, 5-fluouracil, adriamycin, methotrexate, busulfan, chlorambucil, cyclophosphamide, melphalan, nitrogen mustard, nitrosourea, streptokinase, urokinase, alteplase, angiotensin II inhibitor, aldosterone receptor inhibitor, erythropoietin, N-methyl-d-aspartate (NMDA) receptor inhibitor, lovastatin, rapamycin, celebrex, ticlopin, marimastat, and trocade.

The linking between the agent and the peptide of the present invention may be performed by the methods known in the art, such as covalent bonding, cross-linking, and the like. Here, if necessary, the peptides of the present invention may be chemically modified to the extent that the activity thereof is not lost. The amount of the peptide of the present invention included in the composition of the present invention may vary depending on types and amount of therapeutic agents to be bound.

In the composition of the present invention, the peptides of the present invention may be provided in a labeled state for use in determination of the target organ binding, detection, and quantification, as described above.

In one embodiment, the composition of the present invention may be provided in the pure form of the peptide or may be provided through suitable formulation together with a pharmaceutically acceptable carrier.

The term "pharmaceutically acceptable composition" as used herein refers to a physiologically allowable and non-toxic composition that does not normally cause allergic reactions, such as gastrointestinal disorders and dizziness, or similar reactions, when administered to humans. Examples of the carrier include all types of solvents, dispersion media, oil-in-water or water-in-oil emulsions, aqueous compositions, liposomes, microbeads and microsomes, and biodegradable nanoparticles.

In one or more embodiments, the composition of the present invention may be formulated together with a suitable carrier according to the route of administration. The administration route of the composition of the present invention may include, although not limited thereto, an oral or parenteral administration route. Examples of the parenteral administration route include transdermal, nasal, peritoneal, muscular, subcutaneous, and intravenous routes.

When the composition of the present invention is orally administered, the composition of the present invention may be formulated together with a suitable oral administration carrier, in the form of powder, granule, tablet, pill, refined sugar, capsule, liquid, gel, syrup, suspension, water, and the like, according to the methods known in the art. Examples of the suitable oral administration carrier include sugars, such as lactose, dextrose, sucrose, sorbitol, mannitol, xylitol, erythritol, and malitol; starch, such as corn starch, wheat starch, rice starch, and potato starch; cellulose type, such as cellulose, methylcellulose, sodium carboxymethylcellulose, and hydroxypropylmethyl cellulose; and fillers, such as gelatin, polyvinylpyrrolidone. In addition, as needed, cross-linked polyvinylpyrrolidone, agar, alginic acid, or sodium alginate may be added as a disintergrant. Furthermore, the composition of the present invention may further include an anti-coagulant, a lubricant, a wetting agent, a flavoring agent, an emulsifier, and an antiseptic agent.

In addition, when the composition of the present invention is parenterally administered, the composition of the present invention may be formulated together with a suitable parenteral administration carrier, in the form of injections, transdermal drugs, and nasal inhalants, according to the methods known in the art. In the case of injections, the injections must be sterilized and protected against contamination of microorganisms, such as bacteria and fungi. In the case of injections, examples of the suitable parenteral administration carrier include, although not limited thereto, water, ethanol, polyol (for example, glycerol, propylene glycol, and liquid polyethylene glycol), and a mixture thereof, and/or a solvent or dispersion medium containing plant oil. More particularly, the suitable parenteral administration carrier may be isotonic solution, such as Hanks' solution, Ringer's solution, phosphate buffered saline (PBS) containing triethanol amine) or sterilized water for injection, 10% ethanol, 40% propylene glycol, and 5% dextrose. To protect the injections against contamination of microorganisms, various antimicrobial and antifungal agents, such as parabene, chlorobutanol, phenol, sorbic acid, and thimerosal, may be further added. In addition, in most cases of the injections, sugar or isotonic agent, such as sodium chloride, may be further included. These formulations are described in the document (Remington's Pharmaceutical Science, 15th Edition, 1975, Mack Publishing Company, Easton, Pa.).

In the case of an inhalation administration agent, compounds used in accordance with the present invention may be conveniently delivered in the form of an aerosol spray from a pressed pack or fog machine by using suitable propellants, such as dichlorofluoromethane, trichlorofluoromethane, dichlorotetrafluoroethane, carbon dioxide, or other suitable gases. In the case of pressed aerosol, a dosage unit may be determined by providing a valve that delivers a measured amount. For example, a gelatin capsule and a cartridge used in an inhaler or insufflators may be formulated to contain a compound and a powder mixture of suitable powder bases such as lactose or starch.

Other pharmaceutically acceptable carriers can be referred by the description in the following reference (Remington's Pharmaceutical Sciences, 19th ed., Mack Publishing Company, Easton, Pa., 1995).

In addition, the composition of the present invention may further include at least one buffer (for example, saline solution or PBS), carbohydrate (for example, glucose, mannose, sucrose, or dextran), stabilizers (for example, sodium bisulfate or ascorbic acid), antioxidants, bacteriostats, chelating agents (for example, EDTA or glutathione), adjuvants (for example, aluminum hydroxide), suspending agents, thickeners and/or preservatives (for example, benzalkonium chloride, methyl- or propyl-paraben and chlorobutanol).

In addition, the composition of the present invention may be formulated by using the methods known in the art, so as to provide rapid, sustained, or delayed release of active ingredients after administration to the mammals.

The composition formulated as described above may be administered through various routes including oral, transdermal, subcutaneous, iravenous, or intramuscular routes, in an effective amount. The term "effective amount" as used herein refers to the amount of substance that, when administered to a patient, enables the tracing of the diagnostic or therapeutic effect. The dosage of the composition of the present invention can be appropriately selected depending on a route of administration, a target of administration, a target disease and severity thereof, and a patient's age, gender, weight, individual differences, and disease state. Preferably, the composition including the peptide of the present invention may include an effective ingredient in a different amount depending on the severity of disease. However, in general, the composition may be administered several times a day, usually with an effective dose of 1 mg to 1,000 mg per administration to adults.

Furthermore, since the peptides of the present invention specifically binds to the tumor cell, a lesion in which cancer is progressing can be imaged in vivo together with any labeling means (imaging means). Accordingly, the present invention provides a composition for imaging a tumor cell, the composition including the peptide as an effective ingredient.

In the present invention, a tumor cell may be a tumor cell caused by K-ras mutation, and more particularly, may refer to a lung cancer cell, a pancreatic cancer cell, a colon cancer cell, a bile duct cancer cell, or a gallbladder cancer cell. More particularly, a tumor cell in the present invention may refer to a lung cancer cell.

The imaging of the tumor cell can be understood by those skilled in the art as imaging and diagnosis of the affected area of tumor disease, and the tumor disease is described above. In detail, for example, the composition for imaging of the present invention may be provided as a composition for detecting a cancer cell, but embodiments of the present invention are not limited thereto.

Here, the imaging and diagnosis of disease may be used, although not limited thereto, for the purpose of the first medical examination of disease, as well as for the monitoring of the progress of disease, the progress of treatment, and the responses to therapeutic agents. The peptides of the present invention may be provided in a labeled state for use in determination of the binding, detection, and quantification, as described above.

The present invention provides a composition for treating cancer, the pharmaceutical composition including, as effective ingredients, a peptide, which consists of any one amino acid sequence selected from the group consisting of SEQ ID NO: 1 to SEQ ID NO: 4, and an anticancer agent binding to the peptide.

As the anticancer agent that can be linked to the peptide of the present invention, types of the anticancer agent are not particularly limited as long as it is a known anticancer agent. The anticancer agent may include at least one selected from the group consisting of paclitaxel, doxorubicin, vincristine, daunorubicin, vinblastine, actinomycin-D, docetaxel, etoposide, teniposide, bisantrene, homoharringtonine, Gleevec (STI-571), cisplain, 5-fluouracil, adriamycin, methotrexate, busulfan, chlorambucil, cyclophosphamide, melphalan, nitrogen mustard, nitrosourea, streptokinase, urokinase, alteplase, angiotensin II inhibitor, aldosterone receptor inhibitor, erythropoietin, N-methyl-d-aspartate (NMDA) receptor inhibitor, lovastatin, rapamycin, celebrex, ticlopin, marimastat, and trocade.

Due to the tumor cell-specific binding capability of the peptides and selective delivery capability of the anticancer agent only to the cells of the diseases area, the efficacy of the drug can be increased, and at the same time, side effects on normal tissues can be significantly reduced.

The peptides and the anticancer agent of the present invention can be linked by a covalent bond, and in particular, may be linked via a linker. However, embodiments of the present invention are not limited thereto.

The present invention provides a method of treating cancer, the method including: administering a desired subject with an effective amount of a peptide targeting a tumor cell and an anticancer agent binding thereto, wherein the peptide consists of any one amino acid sequence selected from the group consisting of SEQ ID NO: 1 to SEQ ID NO: 4.

The present invention provides use of a peptide targeting a tumor cell for preparation of an anticancer agent, the peptide consisting of any one amino acid sequence selected from the group consisting of SEQ ID NO: 1 to SEQ ID NO: 4.

The term "treating or treatment" as used herein refers to a clinical procedure designed to alter the natural course of a subject or cell being treated, and can be performed for the prevention of clinopathology or during the course. Preferred effects of the treatment include inhibition of the occurrence or recurrence of disease, relieve in symptoms, reduction of direct or indirect pathological consequences of disease, inhibition of metastasis, reduction in disease progression rate, improvement of disease state, and moderate or improved prognosis. In one embodiment, the peptides of the present invention may be used to delay the occurrence of disease or disorder, or to delay the progression of disease or disorder.

The term "effective amount" as used herein refers to an amount exhibiting, when administered to a patient, therapeutic and preventive effects of cancer or inhibitory effects on cancer metastasis. The term "subject" as used herein refers to an animal, and preferably, may refer to a mammal particularly including a human, an animal-derived cell, tissue, organ, or the like. The subject may be a patient requiring treatment.

In addition, the compositions of the present invention may include 0.001 wt % to 99.999 wt % of the peptides and 99.999 wt % to 0.001 wt % of the carrier.

Advantageous Effects of the Invention

The present invention relates to a peptide targeting a tumor cell and use of the peptide, and more particularly, to a peptide consisting of SEQ ID NO: 1 to SEQ ID NO: 4 and specifically binding to a tumor cell, a composition including the peptide as an effective ingredient for detecting a tumor cell, a composition including the peptide as an effective ingredient for delivering a drug, and a composition including the peptide as an effective ingredient for imaging. The peptide of the present invention can be used for detection or imaging of a tumor cell in vitro and in vivo by specifically binding to a tumor cell.

DESCRIPTION OF THE DRAWINGS

FIG. 1 is a schematic diagram of a method of producing a K-ras transgenic mouse model.

FIG. 2 shows (A) a schematic diagram of a K-ras$^{LA2}$ mutant allele, (B) a lung tumor lesion image of a 18-week-old K-ras$^{LA2}$ model and a lung image of a control group which is a 18-week-old wild type mouse, and (C) an image of genotyping performed on a K-ras$^{LA2}$ transgenic mouse model and a wild type mouse model.

FIG. 3 is a schematic diagram of a phage displaying method.

FIG. 4 shows (A) a graph showing a titer of phages counted per round during a phage library screening process, and (B) a graph showing a titer of phage clones bound to each tumor-targeting peptide and a tumor.

FIG. 5 is a graph showing the target transfer capability of each tumor-targeting peptide in a K-ras$^{LA2}$ transgenic mouse model and a wild type mouse model.

FIG. 6 shows (A) fluorescent images each taken from lungs, kidneys, and liver separated after a synthesized peptide labeled with Flamma-774 is injected intravenously to a K-ras$^{LA2}$ transgenic mouse tail and the mouse is sacrificed 4 hours, and (B) a graph showing quantitatively quantified data of fluorescence staining that are.

FIG. 7 shows (A) fluorescent images taken from lungs after a peptide, which targets a lung tumor of a K-ras$^{LA2}$ transgenic mouse, and a Flamma675 fluoresce-labeled ribosome are injected intravenously to a K-ras$^{LA2}$ transgenic mouse tail and the mouse is sacrificed 6 hours, (B) fluorescent images taken from heart, liver, kidney, and spleen, (C) a graph showing quantitatively quantified data of fluorescence image, and (D) fluorescence observed by histological analysis using a confocal microscope on lung tumor that is frozen-sectioned.

FIG. 8 shows test results for confirming the administration effect of liposomes (CRQTKN-L-D, SEQ ID NO: 11) labeling tumor-targeting peptides and containing doxorubicin, wherein (A) shows evaluation results of the therapeutic effect of the liposomes by extracting mouse lungs after liposomes are administered to a mouse at the same concentration, wherein the number of mice per group is 5, (B) is a graph comparing the weight of the extracted lungs, and (C) is a graph showing the total number of lung tumors shown in each of the extracted lungs and comparing the number of lung tumors having a size of 3 mm or more for analysis (wherein L-D: doxorubicin-containing liposome; CRQTKN-L-D (SEQ ID NO: 11): doxorubicin-containing liposome labeled with tumor-targeting peptide; and PBS: physiological saline administration).

FIG. 9 shows self-fluorescence (red) of doxorubicin observed using a fluorescence microscope after administering liposomes for 3 weeks and staining nucleic acid (blue) with a DAPI reagent in a lung tissue which is extracted and frozen-sectioned, wherein TUNEL analysis (green) is performed to confirm apoptosis due to doxorubicin transfer into the cells.

BEST MODE

Hereinafter, the present invention will be described in detail.

However, the following examples are illustrative examples of the present invention, and are not intended to limit the scope of the present invention in any way.

<Example 1> Preparation of K-ras$^{LA2}$ transgenic mouse K-ras$^{LA2}$ (genetically, K-ras$^{G12DLA2}$) obtained from MMHCC and NCI/NIH mice was given by Dr. T Jacks (Massachusetts Institute of Technology (MIT)) (see FIG. 1 for description of a mouse model preparation method). A K-ras$^{LA2}$ transgenic mouse was cross-bred with a wild type C57BL/6N mouse, and the genotype information thereof is available at http://mouse.ncifcrf.gov (see FIG. 2). DNA of the mouse was obtained from the mouse tail using a Qiaprep column (produced by Qiagen), and subjected to PCR amplification. Primers K1 and K2 having SEQ ID NO: 9 and SEQ ID NO: 10 in a wild type C57BL/6N mouse and primers K1 and K3 having SEQ ID NO: 9 and SEQ ID NO: 11 in the K-ras$^{LA2}$ transgenic mouse were used for the PCR amplification. Conditions for the PCR amplification included an annealing temperature of 60° C. and 35 amplification cycles. Afterwards, the PCR products were loaded on a 1% agarose gel, and 220 bp and 390 bp of the PCR products were detected in a wild type and a mutant, respectively. Then, a mouse identified as a mutant K-ras$^{LA2}$ mouse was used in the experiment.

<Example 2> Selection of Peptide Having Specificity to K-Ras Transgenic Tumor Cell <2-1> Preparation of Phage Peptide Library To find out peptides specific to the K-ras transgenic tumor cells, the phage peptide display technique was used (Smith, Science, 228:1315-1317, 1985). The phage peptide display is a technique of displaying a peptide consisting of several amino acids to several tens of amino acids on the surface of a bacteriophage. Accordingly, a phage library with up to $10^9$ different peptides can be prepared, and in this regard, it is a useful technique for searching many types of peptides at once to screen peptides specific to a desired tissue or tumor (see FIG. 3).

To prepare a phage peptide library for screening peptides specific to K-ras transgenic tumor cells, oligonucleotides, which encode CX$_7$C peptides having cysteine at both ends and containing optional seven amino acids between both ends, were first randomly synthesized. Then, the synthesized oligonucleotides were cloned into protein genes forming the surface of the T7 415-1b phage by using the T7Select kit available from Novagen Co. to prepare a phage peptide library.

<2-2> Screening of Phage Library

To screen peptides having specificity to K-ras transgenic tumor cells in the T7 CX$_7$C phage library prepared above, a random peptide phage library ($1\times10^{11}$ pfu) were injected into a K-ras$^{LA2}$ transgenic mouse via the tail vein.

After 15 minutes, the tumor was excised from the lungs of the K-ras$^{LA2}$ transgenic mouse, finely ground, and added to a DMEM medium to prepare a cell suspension, which was then passed through a70-M filter (DAKO, Carpinteria, Calif., USA). The phages bound to the tumor were reacted with 1% NP-40 for 10 minutes for separation. Afterwards, the separated phages were recovered by treatment with cultured BL21 host bacteria. The phages that were recovered by the BL21 host bacteria and amplified were injected into a K-ras$^{LA2}$ transgenic mouse via the tail vein. Such a round of the screening of phage library was repeated five times. FIG. 4A shows a titer of phages counted per round. At the final 5$^{th}$ round, the multiplicative decrease of the phage clones increased 162 times the first round. Afterwards, from the 4$^{th}$ round and the 5$^{th}$ rounds, a total of 49 clones were randomly selected for the sequencing.

<2-3> DNA of Phage Clones and Amino Acid Sequencing

DNA inserts of each of the 49 phage clones collected in Example 2-2 were sequenced by an automated DNA sequencer (Genotech Inc., Daegeon and SolGent Inc. Daegu) using a 96 pill primer (New England Biolabs). To find amino acid motifs shared between the common sequences or peptides, amino acid sequences deduced based on the nucleotide sequences were was aligned by using the Clustal W program. To find proteins having significant homology, NCBI BLAST search was performed with respect to peptide sequences. As a result of the sequence analysis of the peptides, four phage clones with high affinity for the K-ras transgenic tumor cells were confirmed, and the peptide sequences thereof were as follows: CKSRKDGAC (4R-3, SEQ ID NO: 1), CMPKRPSSC (4R-16, SEQ ID NO: 2), CRGTAEG (4R-21, SEQ ID NO: 3), and CRQTKN (5R-7, SEQ ID NO: 4).

<2-4> Identification of Binding Capability of Phage Clones to Tumor

FIG. 4B shows selective binding capability of the phage clones to tumor cells, wherein the phage clones have SEQ ID NO: 1 to SEQ ID NO: 4 of Example 2-3 and express peptides. The phage clones that express each of the peptides were administered into the K-ras$^{LA2}$ transgenic mouse, and bound to tumor, and a titer of the phage clones was measured. As a result, it was confirmed that the phage clone labeling the CKSRKDGAC (4R-3, SEQ ID NO: 1) showed the greatest binding capability to the tumor (see FIG. 4B).

<2-5> Peptide Synthesis

Peptides consisting of SEQ ID NO:1 to SEQ ID NO: 4 of the present invention that were synthesized and conjugated with fluorescein isothiocyanate (FITC) by Peptron Co., Ltd. (Daejeon, Korea), or conjugated with near-infrared fluorescent reagent FPI774 in the N-terminal by BioActs Inc. (Inchon, Korea). In addition, as a control group of the present invention, peptides consisting of an NSSSVDK (SEQ ID NO: 12) sequence which is a phage surface protein sequence were prepared and fluorescently labeled in the same manner as the above. Briefly, each peptide was synthesized by the standard Fmoc method, and in the N-terminal of each peptide, FITC or near-infrared fluorescent reagent FPI774 was conjugated. Each peptide was then purified by HPLC.

<Example 3> Analysis of Target Delivery Capability of Peptide Targeting Tumors of K-Ras$^{LA2}$ Transgenic Mouse <3-1> Analysis of Near-Infrared Fluorescence Imaging of Tumor-Targeting Peptide To validate whether the peptides prepared in <Example 2-5> in the present invention were specifically transferred to the tumor cells of the K-ras$^{LA2}$ transgenic mouse, a control peptide and a peptide labeled with FPI774 and having SEQ ID NO: 1 to SEQ ID NO: 4 were injected into the K-ras$^{LA2}$ transgenic mouse and a normal mouse via the tail vein of each mouse. After 4 hours, the mice were sacrificed, and each organ thereof was extracted for the near-infrared fluorescence imaging using the eXplore Optix system (ART Inc, Montreal, Canada).

As shown in FIG. 5, it was confirmed that the peptide consisting of CRQTKN (SEQ ID NO: 4) among the peptides of the present invention was most strongly transferred to the tumors of the K-ras$^{LA2}$ transgenic mouse.

<3-2> Analysis of Target Transfer Capability of FPI774-CRQTKN (SEQ ID NO: 13) Peptide to Tumors of K-Ras$^{LA2}$ Transgenic Mouse To confirm the binding capability of the CRQTKN peptide (SEQ ID NO: 4) to the K-ras tumors, the FPI774-CRQTKN (SEQ ID NO: 13) peptide, which is a peptide labeled with a near-infrared fluorescent reagent FPI774, and a control peptide were administered into a K-ras$^{LA2}$ transgenic mouse and a normal mouse via the tail vein of each mouse.

After 4 hours, the mice were scarified, and each organ thereof was extracted for the near-infrared fluorescence imaging using the eXplore Optix system (ART Inc, Montreal, Canada).

As shown in FIG. 6A, it was observed that the fluorescence of FPI774 was strongly expressed in the lungs of the K-ras$^{LA2}$ transgenic mouse, whereas the fluorescence of FPI774 was not expressed in the normal mouse. That is, it was confirmed that the FPI774-CRQTKN (SEQ ID NO: 13) peptide had targeted the tumors. When comparing the delivery to organs other than the lungs, such as kidney and liver (see FIG. 6B), the fluorescence of FPI774 was not observed in general. In addition, FIG. 6B shows quantitatively quantified data of the results of FIG. 6A.

<Example 4> Analysis of Target Transfer Capability of Tumor-Targeting Peptide-Labeled Liposome to In Vivo Tumors <4-1> Preparation of Liposomes Labeled with FPR675-CRQTKN (SEQ ID NO: 14) Peptide and Liposomes Containing Doxorubicin L-phosphatidylcholine (PC), 1,2-diacyl-sn-glycero-3-phosphoethanolamine-N-[methoxy(polyethylene glycol)-2000] (mPEG2000-DSPE), 1,2-distearoyl-sn-glycero-3-phosphoethanolamine-N-[maleimide(polyethyleneglycol) 2000] (maleimide-PEG2000-DSPE), and 1,2 reagents were purchased from Avanti Polar Lipids Company.

Liposomes were first prepared by solvent-injection and extrusion. First, all lipids (PC, cholesterol, and mPEG2000-DSPE) were dissolved in ethanol at a molar ratio of 6:4:0.5 at 60° C., and then, the mixed solution was mixed with water at a volume ratio of 1:10 at 60° C. to perform hydration for 1 hour. The resulting mixed solution passed through polycarbonate membrane filters (pore size: 0.2 μm) six times, and then, additionally passed through a filter having a pore size of 0.05 μm six times, thereby homogenizing the size of the liposome. Here, the size of the liposome was measured by the dynamic light scattering method, and was 80 nm-120 nm in diameter.

Doxorubicin was contained in a liposome by the conventional remote-loading method using ammonium sulfate. The water component in a liposome solution was 250 mM $(NH_4)_2SO_4$. After the liposomal component was eluted, the liposome was added to a dialysis membrane (molecular weight of 3 k) in a sufficient amount of 10% sucrose solution containing 5 mM NaCl, to thereby remove ammonium sulfate on the surface of the liposome. Then, a doxorubicin HCl solution was added to the liposome solution to have a concentration of 1.5 mg/ml to 2 mg/ml. A method of containing a drug was performed for 1 hour at 60° C., followed by rapid cooling.

To label FPI774 and FPR675 to the liposome, these reagents were mixed with all lipid components in ethanol, and then, were injected to a phosphate buffer solution. Due to the hydrophobic property of these fluorescent reagents, the reagents were each contained in the lipid bilayer of the liposome.

A liposome label with the peptide of the present invention was prepared by a post-insertion method. First, the CRQTKN peptide (SEQ ID NO: 4) was linked to maleimide-PEG2000-DSPE at a ratio of 1:2. Next, the resulting mPEG2000-DSPE-CRQTKN (SEQ ID NO: 15) was reacted with a liposome at 60° C. for 1 hour for the insertion of the liposome. Here, an amount of the labeled peptide was set to be 0 mol % to 3 mol % with respect to the total lipids.

<4-2> Analysis of Delivery Capability of Liposome Labeled with FPR675-CRQTKN (SEQ ID NO: 14) Peptide to Tumor Targets In Vivo Liposomes labeled with the FPR675-CRQTKN (SEQ ID NO: 14) peptide targeting tumors of the K-ras$^{LA2}$ transgenic mouse were first prepared in the same manner as in <Example 3-1>. To validate the effect of the peptide targeting tumors, liposomes labeled with a near-infrared fluorescent reagent FPR675 were administered into a K-ras$^{LA2}$ transgenic mouse via the tail vein thereof. After 6 hours, the mouse was scarified, and each organ including lungs was extracted for the fluorescence imaging.

As shown in FIG. 7A, it was observed that the fluorescence of FPR675 was strongly expressed in the tumors of the K-ras$^{LA2}$ transgenic mouse to which the liposomes labeled with the FPR675-CRQTKN (SEQ ID NO: 14) peptide were injected, whereas the fluorescence of FPR675 was not expressed in a mouse to which the liposomes labeled with the FPR675-CRQTKN (SEQ ID NO: 14) peptide were not injected. That is, it was confirmed that the FPR675-CRQTKN (SEQ ID NO: 14) peptide had targeted the tumors.

In FIG. 7B, through observation of fluorescence in organs other than the lungs, it was confirmed that the fluorescence was not generally observed in the heart, liver, kidney, and spleen. In addition, in the quantitatively quantified data of the fluorescence images as shown in FIG. 7C, the same results are obtained.

In FIG. 7D showing fluorescence observed by histological analysis using a confocal microscope on lung tumor that was frozen-sectioned after the previous fluorescence observation, the same results are obtained in terms of histological validation that the fluorescent signals were strongly expressed in the lung tumor tussle of the mouse to which the peptide-labeled liposomes were injected (see FIG. 7D).

<Example 5> Selective Drug Delivery and Target Therapy Using Peptide-Mediated Liposome Including Doxorubicin To evaluate the drug delivery promotion effect of a peptide-mediated peptide targeting a tumor cell, a liposome labeled with the CRQTKN (SEQ ID NO: 4) peptide, which targets tumor to the surface, and including an anti-cancer agent, doxorubicin, was prepared in the same manner as in <Example 4-1>. A liposomal solution was intravenously injected to a 18-week-old to 20-week-old K-ras transgenic mouse in order that the amount of doxorubicin was 4 mg per body weight (kg) of the mouse (4 mg/kg). The treatment was made twice a week for a total of 6 times in three weeks.

When the liposome labeled with the tumor-targeting peptide (CRQTKN-L-D, SEQ ID NO: 11) was administered as shown in FIG. 8A, significant therapeutic effects were obtained as compared with a case where an unlabeled liposome (L-D) was administered at the same concentration. In addition, FIG. 8B shows that the total weight of the lungs increased due to the increase in the number and size of tumors in a group treated with liposomes labeling no peptide and a group treated with physiological saline, whereas the weight of the lungs significantly reduced in a group target-treated with liposomes labeled with the CRQTKN-L-D (SEQ ID NO: 11) and containing doxorubicin. In FIG. 8C, there was no significant difference in the total number of tumors among the test groups. However, when comparing the number of tumors with tumors larger than 3 mm in size comparison, a group treated with liposomes labeled with the tumor-targeting peptide showed a significant decreased in size, meaning that the targeted treatment was achieved. Here, the numerical data are statistically significant results.

Referring to FIG. 9, after 3 weeks of liposome administration, the extracted lungs were frozen-sectioned. The frozen sections of the extracted lungs in each test group were nuclear-stained (blue) with a DAPI reagent, and self-fluorescence of doxorubicin (red) was observed using a fluorescence microscope, so as to examine the level of drug delivery into the cells. Then, the TUNEL analysis was performed to confirm apoptosis due to the drug delivery into the cells.

As a result, it was observed that, as shown in FIG. 9A, red fluorescence of doxorubicin was much more observed in a group of tissues treated with liposomes labeled with the tumor-targeting peptide, compared to a group treated with control liposomes. Meanwhile, weak fluorescence was observed in a group of tissues treated with control liposomes. In addition, in FIG. 9B, the TUNEL results analyzing apoptosis based on the result of the observed delivery of doxorubicine also showed the increased apoptosis in a group where peptide-labeled liposomes were administered (green fluorescence).

INDUSTRIAL APPLICABILITY

The present invention relates to a peptide targeting a tumor cell and use of the peptide, and more particularly, to a peptide consisting of SEQ ID NO: 1 to SEQ ID NO: 4 and specifically binding to a tumor cell, a composition including the peptide as an effective ingredient for detecting a tumor cell, a composition including the peptide as an effective ingredient for delivering a drug, and a composition including the peptide as an effective ingredient for imaging. The peptide of the present invention can be used for detection or imaging of a tumor cell in vitro and in vivo by specifically binding to a tumor cell. In this regard, the present invention is highly industrially applicable.

The invention claimed is:

1. A peptide targeting a tumor cell, the peptide consisting of any one amino acid sequence selected from the group consisting of SEQ ID NO:1 to SEQ ID NO: 2.

2. A composition for delivering a drug specifically to a tumor cell, the composition including the peptide of claim 1 as an effective ingredient.

3. The composition of claim 2, wherein the drug is any one selected from the group consisting of paclitaxel, doxorubicin, vincristine, daunorubicin, vinblastine, actinomycin-D, docetaxel, etoposide, teniposide, bisantrene, homoharringtonine, imatinib mesylate, cisplain, 5-fluouracil, adriamycin, methotrexate, busulfan, chlorambucil, cyclophosphamide, melphalan, nitrogen mustard, nitrosourea, streptokinase, urokinase, alteplase, angiotensin II inhibitor, aldosterone acceptor inhibitor, erythropoietin, N-methyl-d-aspartate (NMDA) receptor inhibitor, Lovastatin, Rapamycin, Celebrex, Marimastat, and Trocade.

4. A method of detecting a tumor cell, the method comprising:
  (a) mixing a peptide targeting the tumor cell with a sample, the peptide consisting of any one amino acid sequence selected from the group consisting of SEQ ID NO:1 to SEQ ID NO: 4;
  (b) removing the peptide that is unbound or non-specifically bound; and
  (c) determining whether or not the peptide is bound and a binding position of the peptide.

5. The method of claim 4, wherein the tumor cell is caused by K-ras mutation.

6. The method of claim 4, wherein the peptide is labelled with one selected from a chromogenic enzyme, a radioactive isotope, a chromophore, a luminescent material, a fluorescer, a superparamagentic particle, and an ultrasuper paramagentic particle.

7. The method of claim 4, wherein tumor cell is any one selected from the group consisting of a lung tumor cell, a pancreatic cancer cell, a colorectal cancer cell, a biliary tract cancer cell, a gallbladder cancer cell, and a leukemic cell.

8. The method of claim 4, wherein the peptide is labelled with one selected from a chromogenic enzyme, a radioactive isotope, a chromophore, a luminescent material, a fluorescer, a superparamagentic particle, an ultrasuper paramagentic particle, and imaging the tumor cell.

9. A method of selectively delivering a drug to a tumor cell in a subject, comprising:
  preparing a peptide selectively delivering the drug to the tumor cell, the peptide is consisting of any one amino acid sequence selected from the group consisting of SEQ ID NO: 3 to SEQ ID NO: 4; and
  administering the peptide associated with the drug to the subject.

10. The method of claim 9, wherein the drug is any one selected from the group consisting of paclitaxel, doxorubicin, vincristine, daunorubicin, vinblastine, actinomycin-D, docetaxel, etoposide, teniposide, bisantrene, homoharringtonine, imatinib mesylate, cisplain, 5-fluouracil, adriamycin, methotrexate, busulfan, chlorambucil, cyclophosphamide, melphalan, nitrogen mustard, nitrosourea, streptokinase, urokinase, alteplase, angiotensin II inhibitor, aldosterone acceptor inhibitor, erythropoietin, N-methyl-d-aspartate (NMDA) receptor inhibitor, Lovastatin, Rapamycin, Celebrex, Ticlopin, Marimastat, and Trocade.

* * * * *

SEQUENCE LISTING

```
<160> NUMBER OF SEQ ID NOS: 15

<210> SEQ ID NO 1
<211> LENGTH: 9
<212> TYPE: PRT
<213> ORGANISM: Artificial Sequence
<220> FEATURE:
<223> OTHER INFORMATION: 4R-3 peptide

<400> SEQUENCE: 1

Cys Lys Ser Arg Lys Asp Gly Ala Cys
1               5

<210> SEQ ID NO 2
<211> LENGTH: 9
<212> TYPE: PRT
<213> ORGANISM: Artificial Sequence
<220> FEATURE:
<223> OTHER INFORMATION: 4R-16 peptide

<400> SEQUENCE: 2

Cys Met Pro Lys Arg Pro Ser Ser Cys
1               5

<210> SEQ ID NO 3
<211> LENGTH: 7
<212> TYPE: PRT
<213> ORGANISM: Artificial Sequence
<220> FEATURE:
<223> OTHER INFORMATION: 4R-21 peptide

<400> SEQUENCE: 3

Cys Arg Gly Thr Ala Glu Gly
1               5

<210> SEQ ID NO 4
<211> LENGTH: 6
<212> TYPE: PRT
<213> ORGANISM: Artificial Sequence
<220> FEATURE:
<223> OTHER INFORMATION: 5R-7 peptide

<400> SEQUENCE: 4

Cys Arg Gln Thr Lys Asn
1               5

<210> SEQ ID NO 5
```

```
<211> LENGTH: 27
<212> TYPE: DNA
<213> ORGANISM: Artificial Sequence
<220> FEATURE:
<223> OTHER INFORMATION: 4R-3 nucleotide

<400> SEQUENCE: 5
tgcaagtcga ggaaggatgg ggcgtgc                                              27

<210> SEQ ID NO 6
<211> LENGTH: 27
<212> TYPE: DNA
<213> ORGANISM: Artificial Sequence
<220> FEATURE:
<223> OTHER INFORMATION: 4R-16 nucleotide

<400> SEQUENCE: 6
tgcatgccta agcgtccgtc gagttgc                                              27

<210> SEQ ID NO 7
<211> LENGTH: 21
<212> TYPE: DNA
<213> ORGANISM: Artificial Sequence
<220> FEATURE:
<223> OTHER INFORMATION: 4R-21 nucleotide

<400> SEQUENCE: 7
tgcaggggta ctgctgaggg g                                                    21

<210> SEQ ID NO 8
<211> LENGTH: 18
<212> TYPE: DNA
<213> ORGANISM: Artificial Sequence
<220> FEATURE:
<223> OTHER INFORMATION: 5R-7 nucleotide

<400> SEQUENCE: 8
tgccgtcaga ctaagaat                                                        18

<210> SEQ ID NO 9
<211> LENGTH: 20
<212> TYPE: DNA
<213> ORGANISM: Artificial Sequence
<220> FEATURE:
<223> OTHER INFORMATION: K1 primer

<400> SEQUENCE: 9
tgcacagctt agtgagaccc                                                      20

<210> SEQ ID NO 10
<211> LENGTH: 20
<212> TYPE: DNA
<213> ORGANISM: Artificial Sequence
<220> FEATURE:
<223> OTHER INFORMATION: K2 primer

<400> SEQUENCE: 10
gactgctctc tttcacctcc                                                      20

<210> SEQ ID NO 11
<211> LENGTH: 6
<212> TYPE: PRT
<213> ORGANISM: Artificial Sequence
<220> FEATURE:
<223> OTHER INFORMATION: 5R-7 peptide with L-D (doxorubicin-containing
      liposome)
<220> FEATURE:
```

```
<221> NAME/KEY: MISC_FEATURE
<222> LOCATION: (6)..(6)
<223> OTHER INFORMATION: Modified at C-terminus by L-D (doxorubicin-
      containing liposome)

<400> SEQUENCE: 11

Cys Arg Gln Thr Lys Asn
1               5

<210> SEQ ID NO 12
<211> LENGTH: 7
<212> TYPE: PRT
<213> ORGANISM: Artificial Sequence
<220> FEATURE:
<223> OTHER INFORMATION: Control peptide

<400> SEQUENCE: 12

Asn Ser Ser Ser Val Asp Lys
1               5

<210> SEQ ID NO 13
<211> LENGTH: 6
<212> TYPE: PRT
<213> ORGANISM: Artificial Sequence
<220> FEATURE:
<223> OTHER INFORMATION: 5R-7 peptide with near-infrared fluorescent
      reagent FPI774
<220> FEATURE:
<221> NAME/KEY: MISC_FEATURE
<222> LOCATION: (1)..(1)
<223> OTHER INFORMATION: Modified at N-terminus by near-infrared
      fluorescent reagent FPI774

<400> SEQUENCE: 13

Cys Arg Gln Thr Lys Asn
1               5

<210> SEQ ID NO 14
<211> LENGTH: 6
<212> TYPE: PRT
<213> ORGANISM: Artificial Sequence
<220> FEATURE:
<223> OTHER INFORMATION: 5R-7 peptide with near-infrared fluorescent
      reagent FPR675
<220> FEATURE:
<221> NAME/KEY: MISC_FEATURE
<222> LOCATION: (1)..(1)
<223> OTHER INFORMATION: Modified at N-terminus by near-infrared
      fluorescent reagent FPR675

<400> SEQUENCE: 14

Cys Arg Gln Thr Lys Asn
1               5

<210> SEQ ID NO 15
<211> LENGTH: 6
<212> TYPE: PRT
<213> ORGANISM: Artificial Sequence
<220> FEATURE:
<223> OTHER INFORMATION: 5R-7 peptide with
      1,2-diacyl-sn-glycero-3-phosphoethanolamine-N-[methoxy(polyethyle
      ne glycol)-2000] (mPEG2000-DSPE)
<220> FEATURE:
<221> NAME/KEY: MISC_FEATURE
<222> LOCATION: (1)..(1)
<223> OTHER INFORMATION: Modified at N-terminus by
      1,2-diacyl-sn-glycero-3-phosphoethanolamine-N-[methoxy(polyethyle
      ne glycol)-2000] (mPEG2000-DSPE)
```

```
<400> SEQUENCE: 15

Cys Arg Gln Thr Lys Asn
1               5
```